United States Patent
Stack et al.

(10) Patent No.: US 9,314,361 B2
(45) Date of Patent: Apr. 19, 2016

(54) SYSTEM AND METHOD FOR ANCHORING STOMACH IMPLANT

(75) Inventors: Richard S. Stack, Chapel Hill, NC (US); William L. Athas, Chapel Hill, NC (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1615 days.

(21) Appl. No.: 11/901,023

(22) Filed: Sep. 14, 2007

(65) Prior Publication Data

US 2008/0208355 A1   Aug. 28, 2008

Related U.S. Application Data

(60) Provisional application No. 60/844,823, filed on Sep. 15, 2006.

(51) Int. Cl.
*A61B 17/08* (2006.01)
*A61B 17/10* (2006.01)
(Continued)

(52) U.S. Cl.
CPC ........... *A61F 5/0003* (2013.01); *A61B 17/0401* (2013.01); *A61B 17/064* (2013.01); *A61F 5/0036* (2013.01); *A61F 5/0069* (2013.01); *A61B 2017/0404* (2013.01); *A61B 2017/0409* (2013.01); *A61B 2017/0412* (2013.01);
(Continued)

(58) Field of Classification Search
CPC .............. A61B 2017/0464; A61B 2017/0409; A61B 17/0401; A61B 2017/0412; A61B 2017/0437; A61F 5/0003; A61F 5/0036; A61F 5/0069; A61F 5/003; A61F 5/0013; A61F 5/0083; A61F 5/0089

USPC ......... 606/151, 153, 191, 192, 198, 142, 143; 623/23.64, 23.65; 600/37
See application file for complete search history.

(56) References Cited

U.S. PATENT DOCUMENTS 1,408,865 A   3/1922   Cowell
3,663,965 A   5/1972   Lee et al.
(Continued)

FOREIGN PATENT DOCUMENTS

AU   629664   2/1991
DE   08708978 U1   11/1987
(Continued)

OTHER PUBLICATIONS

International Search report and Written Opinion for PCT application PCT/US2007/019940, Mar. 20, 2008, 12 pages (2008).
(Continued)

*Primary Examiner* — Christopher L Templeton
(74) *Attorney, Agent, or Firm* — Bookoff McAndrews, PLLC

(57) ABSTRACT

A gastric implant system includes a gastric implant such as a restrictive pouch or a gastric balloon, an anchor passable through the mouth and stomach and further through the stomach wall into engagement with abdominal wall tissue. When the anchor is engaged to abdominal wall tissue, the stomach wall and abdominal wall are brought into contact with one another such that a proximal portion of the anchor extends into the stomach interior while a distal portion of the anchor remains engaged to the abdominal wall. A locking element coupled to the proximal section of the anchor is sued to maintain contact between the stomach wall and abdominal wall. The gastric implant is advanced through the oral cavity into the stomach and is coupled to the anchor.

12 Claims, 3 Drawing Sheets

(51) Int. Cl.
*A61M 29/00* (2006.01)
*A61F 5/00* (2006.01)
*A61B 17/064* (2006.01)
*A61B 17/04* (2006.01)

(52) U.S. Cl.
CPC . *A61B2017/0437* (2013.01); *A61B 2017/0464* (2013.01); *A61B 2017/0647* (2013.01); *A61F 5/0013* (2013.01)

(56) References Cited

U.S. PATENT DOCUMENTS

| | | |
|---|---|---|
| 4,134,405 A | 1/1979 | Smit |
| 4,207,890 A | 6/1980 | Mamajek et al. |
| 4,246,893 A | 1/1981 | Berson |
| 4,315,509 A | 2/1982 | Smit |
| 4,331,277 A | 5/1982 | Green |
| 4,403,604 A | 9/1983 | Wilkinson et al. |
| 4,416,267 A | 11/1983 | Garren et al. |
| 4,417,360 A | 11/1983 | Moasser |
| 4,441,215 A | 4/1984 | Kaster |
| 4,467,804 A | 8/1984 | Hardy et al. |
| 4,485,805 A | 12/1984 | Foster, Jr. |
| 4,501,264 A | 2/1985 | Rockey |
| 4,607,618 A | 8/1986 | Angelchik |
| 4,612,933 A | 9/1986 | Brinkerhoff et al. |
| 4,617,932 A | 10/1986 | Kornberg |
| 4,641,653 A | 2/1987 | Rockey |
| 4,648,383 A | 3/1987 | Angelchik |
| 4,694,827 A | 9/1987 | Weiner et al. |
| 4,723,547 A | 2/1988 | Kullas et al. |
| 4,747,849 A | 5/1988 | Galtier |
| 4,846,836 A | 7/1989 | Reich |
| 4,848,367 A | 7/1989 | Avant et al. |
| 4,899,747 A | 2/1990 | Garren et al. |
| 4,925,446 A | 5/1990 | Garay et al. |
| 4,946,440 A | 8/1990 | Hall |
| 4,969,896 A | 11/1990 | Shors |
| 4,997,084 A | 3/1991 | Opie et al. |
| 5,006,106 A | 4/1991 | Angelchik |
| 5,037,021 A | 8/1991 | Mills et al. |
| 5,061,275 A | 10/1991 | Wallsten et al. |
| 5,084,061 A | 1/1992 | Gau et al. |
| 5,088,979 A | 2/1992 | Filipi et al. |
| 5,163,952 A | 11/1992 | Froix |
| 5,211,658 A | 5/1993 | Clouse |
| 5,234,454 A | 8/1993 | Bangs |
| 5,246,456 A | 9/1993 | Wilkinson |
| 5,259,399 A | 11/1993 | Brown |
| 5,263,629 A | 11/1993 | Trumbull et al. |
| 5,290,217 A | 3/1994 | Campos |
| 5,306,300 A | 4/1994 | Berry |
| 5,314,473 A | 5/1994 | Godin |
| 5,327,914 A | 7/1994 | Shlain |
| 5,345,949 A | 9/1994 | Shain |
| 5,355,897 A | 10/1994 | Pietrafitta et al. |
| 5,370,661 A * | 12/1994 | Branch .................. 606/232 |
| 5,401,241 A | 3/1995 | Delany |
| 5,403,326 A | 4/1995 | Harrison et al. |
| 5,405,377 A | 4/1995 | Cragg |
| 5,431,673 A | 7/1995 | Summers et al. |
| 5,486,187 A | 1/1996 | Schenck |
| 5,514,176 A | 5/1996 | Bosley, Jr. |
| 5,535,935 A | 7/1996 | Vidal et al. |
| 5,542,949 A | 8/1996 | Yoon |
| 5,562,239 A | 10/1996 | Boiarski et al. |
| 5,571,116 A | 11/1996 | Bolanos et al. |
| 5,577,654 A | 11/1996 | Bishop |
| 5,593,434 A | 1/1997 | Williams |
| 5,597,107 A | 1/1997 | Knodel et al. |
| 5,609,624 A | 3/1997 | Kalis |
| 5,628,786 A | 5/1997 | Banas et al. |
| 5,630,539 A | 5/1997 | Plyley et al. |
| 5,647,526 A | 7/1997 | Green et al. |
| 5,653,743 A | 8/1997 | Martin |
| 5,662,713 A | 9/1997 | Andersen et al. |
| 5,673,841 A | 10/1997 | Schulze et al. |
| 5,674,241 A | 10/1997 | Bley et al. |
| 5,706,998 A | 1/1998 | Plyley et al. |
| 5,709,657 A | 1/1998 | Zimmon |
| 5,720,776 A | 2/1998 | Chuter et al. |
| 5,749,918 A | 5/1998 | Hogendijk et al. |
| 5,762,255 A | 6/1998 | Chrisman et al. |
| 5,771,903 A | 6/1998 | Jakobsson |
| 5,785,684 A | 7/1998 | Zimmon |
| 5,820,584 A | 10/1998 | Crabb |
| 5,839,639 A | 11/1998 | Sauer et al. |
| 5,848,964 A | 12/1998 | Samuels |
| 5,855,311 A | 1/1999 | Hamblin et al. |
| 5,855,601 A | 1/1999 | Bessler et al. |
| 5,856,445 A | 1/1999 | Korsmeyer |
| 5,861,036 A | 1/1999 | Godin |
| 5,868,141 A | 2/1999 | Ellias |
| 5,887,594 A | 3/1999 | LoCicero, III |
| 5,897,562 A | 4/1999 | Bolanos et al. |
| 5,910,144 A | 6/1999 | Hayashi |
| 5,922,019 A | 7/1999 | Hankh et al. |
| 5,947,983 A | 9/1999 | Solar et al. |
| 5,993,473 A | 11/1999 | Chan et al. |
| 5,993,483 A | 11/1999 | Gianotti |
| 6,016,848 A | 1/2000 | Egres, Jr. |
| 6,051,015 A | 4/2000 | Maahs |
| 6,086,600 A | 7/2000 | Kortenback |
| 6,098,629 A | 8/2000 | Johnson et al. |
| 6,102,922 A | 8/2000 | Jakobsson et al. |
| 6,113,609 A | 9/2000 | Adams |
| 6,120,534 A | 9/2000 | Ruiz |
| 6,146,416 A | 11/2000 | Andersen et al. |
| 6,159,146 A | 12/2000 | El Gazayerli |
| 6,159,238 A | 12/2000 | Killion et al. |
| 6,197,022 B1 | 3/2001 | Baker |
| 6,206,930 B1 | 3/2001 | Burg et al. |
| 6,245,088 B1 | 6/2001 | Lowery |
| 6,251,132 B1 | 6/2001 | Ravenscroft et al. |
| 6,254,642 B1 | 7/2001 | Taylor |
| 6,258,120 B1 | 7/2001 | McKenzie et al. |
| 6,264,700 B1 | 7/2001 | Kilcoyne et al. |
| 6,287,334 B1 | 9/2001 | Moll et al. |
| 6,302,917 B1 | 10/2001 | Dua et al. |
| 6,358,197 B1 | 3/2002 | Silverman |
| 6,416,522 B1 | 7/2002 | Strecker |
| 6,425,916 B1 | 7/2002 | Garrison et al. |
| 6,454,785 B2 * | 9/2002 | De Hoyos Garza .......... 606/192 |
| 6,460,543 B1 | 10/2002 | Forsell |
| 6,461,366 B1 | 10/2002 | Seguin |
| 6,494,888 B1 | 12/2002 | Laufer et al. |
| 6,494,895 B2 | 12/2002 | Addis |
| 6,503,264 B1 | 1/2003 | Birk |
| 6,506,196 B1 | 1/2003 | Laufer et al. |
| 6,527,784 B2 | 3/2003 | Adams et al. |
| 6,540,789 B1 | 4/2003 | Silverman et al. |
| 6,544,291 B2 | 4/2003 | Taylor |
| 6,547,801 B1 | 4/2003 | Dargent et al. |
| 6,558,400 B2 | 5/2003 | Deem et al. |
| 6,558,429 B2 | 5/2003 | Taylor et al. |
| 6,572,627 B2 | 6/2003 | Gabbay |
| 6,572,629 B2 | 6/2003 | Kalloo |
| 6,575,896 B2 | 6/2003 | Silverman |
| 6,592,596 B1 | 7/2003 | Geitz |
| 6,596,023 B1 | 7/2003 | Nunez et al. |
| 6,607,555 B2 | 8/2003 | Patterson et al. |
| 6,627,206 B2 | 9/2003 | Lloyd |
| 6,632,227 B2 | 10/2003 | Adams |
| 6,663,639 B1 | 12/2003 | Laufer et al. |
| 6,675,809 B2 | 1/2004 | Stack et al. |
| 6,733,512 B2 | 5/2004 | McGhan |
| 6,740,098 B2 | 5/2004 | Abrams et al. |
| 6,740,121 B2 | 5/2004 | Geitz |
| 6,746,460 B2 | 6/2004 | Gannoe et al. |
| 6,755,869 B2 | 6/2004 | Geitz |
| 6,764,518 B2 | 7/2004 | Godin |
| 6,773,440 B2 | 8/2004 | Gannoe et al. |
| 6,773,441 B1 | 8/2004 | Laufer et al. |
| 6,790,214 B2 | 9/2004 | Kraemer et al. |

(56) References Cited

U.S. PATENT DOCUMENTS

| | | |
|---|---|---|
| 6,790,237 B2 | 9/2004 | Stinson |
| 6,821,285 B2 | 11/2004 | Laufer et al. |
| 6,835,200 B2 | 12/2004 | Laufer et al. |
| 6,845,776 B2 | 1/2005 | Stack et al. |
| 6,916,332 B2 | 7/2005 | Adams |
| 6,932,838 B2 | 8/2005 | Schwartz et al. |
| 6,960,233 B1 | 11/2005 | Berg et al. |
| 6,966,875 B1 | 11/2005 | Longobardi |
| 6,981,978 B2 | 1/2006 | Gannoe |
| 6,981,980 B2 | 1/2006 | Sampson et al. |
| 6,994,715 B2 | 2/2006 | Gannoe et al. |
| 7,011,094 B2 | 3/2006 | Rapackie et al. |
| 7,020,531 B1 | 3/2006 | Colliou et al. |
| 7,025,791 B2 | 4/2006 | Levine et al. |
| 7,033,373 B2 | 4/2006 | de la Torre et al. |
| 7,033,384 B2 | 4/2006 | Gannoe et al. |
| 7,037,344 B2 | 5/2006 | Kagan et al. |
| 7,056,305 B2 | 6/2006 | Garza |
| 7,066,945 B2 | 6/2006 | Hashiba et al. |
| 7,083,629 B2 | 8/2006 | Weller et al. |
| 7,090,699 B2 | 8/2006 | Geitz |
| 7,097,650 B2 | 8/2006 | Weller et al. |
| 7,097,665 B2 | 8/2006 | Stack et al. |
| 7,111,627 B2 | 9/2006 | Stack et al. |
| 7,112,186 B2 | 9/2006 | Shah |
| 7,120,498 B2 | 10/2006 | Imran et al. |
| 7,121,283 B2 | 10/2006 | Stack et al. |
| 7,146,984 B2 | 12/2006 | Stack et al. |
| 7,147,140 B2 | 12/2006 | Wukusick et al. |
| 7,152,607 B2 | 12/2006 | Stack et al. |
| 7,160,312 B2 | 1/2007 | Saadat et al. |
| 7,172,613 B2 | 2/2007 | Wazne |
| 7,175,638 B2 | 2/2007 | Gannoe et al. |
| 7,175,660 B2 | 2/2007 | Cartledge et al. |
| 7,211,114 B2 | 5/2007 | Bessler et al. |
| 7,214,233 B2 | 5/2007 | Gannoe et al. |
| 7,220,237 B2 | 5/2007 | Gannoe et al. |
| 7,220,284 B2 | 5/2007 | Kagan et al. |
| 7,223,277 B2 | 5/2007 | DeLegge |
| 7,229,428 B2 | 6/2007 | Gannoe et al. |
| 7,229,453 B2 | 6/2007 | Anderson et al. |
| 7,255,675 B2 | 8/2007 | Gertner et al. |
| 7,261,722 B2 | 8/2007 | McGuckin, Jr. et al. |
| 7,288,101 B2 | 10/2007 | Deem et al. |
| 7,306,614 B2 | 12/2007 | Weller et al. |
| 7,315,509 B2 | 1/2008 | Jeong et al. |
| 7,316,716 B2 | 1/2008 | Egan |
| 7,320,696 B2 | 1/2008 | Gazi et al. |
| 7,326,207 B2 | 2/2008 | Edwards |
| 7,335,210 B2 | 2/2008 | Smit |
| 7,347,863 B2 | 3/2008 | Rothe et al. |
| 7,347,875 B2 | 3/2008 | Levine et al. |
| 7,354,454 B2 | 4/2008 | Stack et al. |
| 7,399,304 B2 | 7/2008 | Gambale et al. |
| 7,431,725 B2 | 10/2008 | Stack et al. |
| 7,461,767 B2 | 12/2008 | Viola et al. |
| 7,470,251 B2 | 12/2008 | Shah |
| 7,485,142 B2 | 2/2009 | Milo |
| 7,503,922 B2 | 3/2009 | Deem et al. |
| 7,520,884 B2 | 4/2009 | Swanstrom et al. |
| 7,575,586 B2 | 8/2009 | Berg et al. |
| 7,608,114 B2 | 10/2009 | Levine et al. |
| 7,615,064 B2 | 11/2009 | Bjerken |
| 7,628,821 B2 | 12/2009 | Stack et al. |
| 7,662,161 B2 | 2/2010 | Briganti et al. |
| 7,670,279 B2 | 3/2010 | Gertner |
| 7,674,271 B2 | 3/2010 | Bjerken |
| 7,695,446 B2 | 4/2010 | Levine et al. |
| 7,699,863 B2 | 4/2010 | Marco et al. |
| 7,708,181 B2 | 5/2010 | Cole et al. |
| 7,717,843 B2 | 5/2010 | Balbierz et al. |
| 7,721,932 B2 | 5/2010 | Cole et al. |
| 7,731,757 B2 | 6/2010 | Taylor et al. |
| 7,744,613 B2 | 6/2010 | Ewers et al. |
| 7,744,627 B2 | 6/2010 | Orban et al. |
| 7,753,870 B2 | 7/2010 | Demarais et al. |
| 7,766,861 B2 | 8/2010 | Levine et al. |
| 7,819,836 B2 | 10/2010 | Levine et al. |
| 7,846,138 B2 | 12/2010 | Dann et al. |
| 7,846,174 B2 | 12/2010 | Baker et al. |
| 7,846,179 B2 * | 12/2010 | Belef et al. ............... 606/222 |
| 7,881,797 B2 | 2/2011 | Griffin et al. |
| 7,892,214 B2 | 2/2011 | Kagan et al. |
| 7,892,292 B2 | 2/2011 | Stack et al. |
| 2001/0011543 A1 | 8/2001 | Forsell |
| 2001/0020189 A1 | 9/2001 | Taylor |
| 2001/0020190 A1 | 9/2001 | Taylor |
| 2001/0021796 A1 | 9/2001 | Silverman et al. |
| 2001/0037130 A1 * | 11/2001 | Adams ..................... 606/220 |
| 2001/0044595 A1 | 11/2001 | Reydel et al. |
| 2002/0022851 A1 | 2/2002 | Kalloo et al. |
| 2002/0055757 A1 * | 5/2002 | Torre et al. ............... 606/192 |
| 2002/0072761 A1 | 6/2002 | Abrams et al. |
| 2002/0082621 A1 | 6/2002 | Schurr et al. |
| 2002/0099439 A1 | 7/2002 | Schwartz et al. |
| 2002/0183767 A1 | 12/2002 | Adams et al. |
| 2002/0183768 A1 | 12/2002 | Deem et al. |
| 2002/0188354 A1 | 12/2002 | Peghini |
| 2003/0009236 A1 | 1/2003 | Godin |
| 2003/0040804 A1 | 2/2003 | Stack et al. |
| 2003/0040808 A1 | 2/2003 | Stack et al. |
| 2003/0065359 A1 | 4/2003 | Weller et al. |
| 2003/0093117 A1 | 5/2003 | Saadat |
| 2003/0109892 A1 | 6/2003 | Deem et al. |
| 2003/0109931 A1 | 6/2003 | Geitz |
| 2003/0120289 A1 | 6/2003 | McGuckin, Jr. et al. |
| 2003/0158569 A1 | 8/2003 | Wazne |
| 2003/0191476 A1 | 10/2003 | Smit |
| 2003/0191525 A1 | 10/2003 | Thornton |
| 2003/0199989 A1 | 10/2003 | Stack et al. |
| 2003/0199990 A1 | 10/2003 | Stack et al. |
| 2003/0199991 A1 | 10/2003 | Stack et al. |
| 2003/0208209 A1 | 11/2003 | Gambale et al. |
| 2003/0220660 A1 * | 11/2003 | Kortenbach et al. ......... 606/151 |
| 2004/0006351 A1 | 1/2004 | Gannoe et al. |
| 2004/0024386 A1 | 2/2004 | Deem et al. |
| 2004/0030347 A1 | 2/2004 | Gannoe et al. |
| 2004/0044353 A1 | 3/2004 | Gannoe |
| 2004/0044354 A1 | 3/2004 | Gannoe et al. |
| 2004/0044357 A1 | 3/2004 | Gannoe et al. |
| 2004/0044364 A1 * | 3/2004 | DeVries ............ A61B 17/064 606/213 |
| 2004/0059289 A1 * | 3/2004 | Garza Alvarez ........... 604/96.01 |
| 2004/0068276 A1 | 4/2004 | Golden et al. |
| 2004/0082963 A1 | 4/2004 | Gannoe et al. |
| 2004/0088023 A1 | 5/2004 | Imran et al. |
| 2004/0092892 A1 | 5/2004 | Kagan et al. |
| 2004/0092974 A1 | 5/2004 | Gannoe et al. |
| 2004/0093091 A1 * | 5/2004 | Gannoe et al. ............. 623/23.65 |
| 2004/0098043 A1 | 5/2004 | Trout |
| 2004/0107004 A1 | 6/2004 | Levine et al. |
| 2004/0117031 A1 | 6/2004 | Stack et al. |
| 2004/0122456 A1 * | 6/2004 | Saadat ............ A61B 17/00234 606/157 |
| 2004/0133219 A1 | 7/2004 | Forsell |
| 2004/0138761 A1 | 7/2004 | Stack et al. |
| 2004/0143342 A1 | 7/2004 | Stack et al. |
| 2004/0148034 A1 | 7/2004 | Kagan et al. |
| 2004/0153167 A1 | 8/2004 | Stack et al. |
| 2004/0158331 A1 | 8/2004 | Stack et al. |
| 2004/0162568 A1 | 8/2004 | Saadat et al. |
| 2004/0172141 A1 | 9/2004 | Stack et al. |
| 2004/0172142 A1 | 9/2004 | Stack et al. |
| 2004/0186502 A1 | 9/2004 | Sampson et al. |
| 2004/0210243 A1 | 10/2004 | Gannoe et al. |
| 2004/0215216 A1 | 10/2004 | Gannoe et al. |
| 2004/0220682 A1 | 11/2004 | Levine et al. |
| 2004/0225183 A1 | 11/2004 | Michlitsch et al. |
| 2004/0225305 A1 | 11/2004 | Ewers et al. |
| 2004/0236419 A1 | 11/2004 | Milo |
| 2004/0243152 A1 | 12/2004 | Taylor et al. |
| 2004/0243223 A1 | 12/2004 | Kraemer et al. |
| 2004/0260317 A1 * | 12/2004 | Bloom et al. ................. 606/151 |
| 2004/0267378 A1 | 12/2004 | Gazi et al. |

(56) References Cited

U.S. PATENT DOCUMENTS

| | | |
|---|---|---|
| 2005/0004430 A1 | 1/2005 | Lee et al. |
| 2005/0004681 A1 | 1/2005 | Stack et al. |
| 2005/0033326 A1 | 2/2005 | Briganti et al. |
| 2005/0033345 A1 | 2/2005 | DeLegge |
| 2005/0049718 A1 | 3/2005 | Dann et al. |
| 2005/0075654 A1 | 4/2005 | Kelleher |
| 2005/0080444 A1 | 4/2005 | Kraemer et al. |
| 2005/0085787 A1 | 4/2005 | Laufer et al. |
| 2005/0096673 A1 | 5/2005 | Stack et al. |
| 2005/0096750 A1 | 5/2005 | Kagan et al. |
| 2005/0143760 A1* | 6/2005 | Imran ............ 606/142 |
| 2005/0143784 A1* | 6/2005 | Imran ............ 607/40 |
| 2005/0149114 A1 | 7/2005 | Cartledge et al. |
| 2005/0159769 A1 | 7/2005 | Alverdy |
| 2005/0177181 A1 | 8/2005 | Kagan et al. |
| 2005/0183732 A1 | 8/2005 | Edwards |
| 2005/0192599 A1 | 9/2005 | Demarais |
| 2005/0192615 A1 | 9/2005 | Torre et al. |
| 2005/0216040 A1 | 9/2005 | Gertner et al. |
| 2005/0216042 A1 | 9/2005 | Gertner |
| 2005/0228504 A1 | 10/2005 | Demarais et al. |
| 2005/0240279 A1 | 10/2005 | Kagan et al. |
| 2005/0245965 A1 | 11/2005 | Orban et al. |
| 2005/0247320 A1 | 11/2005 | Stack et al. |
| 2005/0250980 A1 | 11/2005 | Swanstrom et al. |
| 2005/0251158 A1 | 11/2005 | Saadat et al. |
| 2005/0251162 A1 | 11/2005 | Rothe et al. |
| 2005/0256533 A1 | 11/2005 | Roth et al. |
| 2005/0256587 A1 | 11/2005 | Egan |
| 2005/0261712 A1 | 11/2005 | Balbierz et al. |
| 2005/0267405 A1 | 12/2005 | Shah |
| 2005/0267499 A1 | 12/2005 | Stack et al. |
| 2005/0267595 A1 | 12/2005 | Chen et al. |
| 2005/0267596 A1 | 12/2005 | Chen et al. |
| 2005/0273060 A1 | 12/2005 | Levy et al. |
| 2006/0015006 A1 | 1/2006 | Laurence et al. |
| 2006/0020247 A1* | 1/2006 | Kagan et al. ............ 604/264 |
| 2006/0020276 A1* | 1/2006 | Saadat et al. ....... A61B 17/0401 606/153 |
| 2006/0020278 A1 | 1/2006 | Burnett et al. |
| 2006/0058829 A1 | 3/2006 | Sampson et al. |
| 2006/0129094 A1 | 6/2006 | Shah |
| 2006/0151568 A1 | 7/2006 | Weller et al. |
| 2006/0155259 A1 | 7/2006 | MacLay |
| 2006/0155311 A1 | 7/2006 | Hashiba et al. |
| 2006/0178560 A1 | 8/2006 | Saadat et al. |
| 2006/0178691 A1 | 8/2006 | Binmoeller |
| 2006/0195139 A1 | 8/2006 | Gertner |
| 2006/0207606 A1* | 9/2006 | Roue et al. ............ 128/848 |
| 2006/0253142 A1 | 11/2006 | Bjerken |
| 2006/0271076 A1 | 11/2006 | Weller et al. |
| 2006/0282095 A1 | 12/2006 | Stokes et al. |
| 2006/0287734 A1 | 12/2006 | Stack et al. |
| 2007/0010864 A1 | 1/2007 | Dann et al. |
| 2007/0027548 A1 | 2/2007 | Levine et al. |
| 2007/0032800 A1 | 2/2007 | Ortiz et al. |
| 2007/0043384 A1 | 2/2007 | Ortiz et al. |
| 2007/0055292 A1 | 3/2007 | Ortiz et al. |
| 2007/0060932 A1 | 3/2007 | Stack et al. |
| 2007/0149994 A1 | 6/2007 | Sosnowski et al. |
| 2007/0175488 A1 | 8/2007 | Cox et al. |
| 2007/0191870 A1 | 8/2007 | Baker et al. |
| 2007/0191871 A1 | 8/2007 | Baker et al. |
| 2007/0198074 A1 | 8/2007 | Dann et al. |
| 2007/0219571 A1 | 9/2007 | Balbierz et al. |
| 2007/0239284 A1 | 10/2007 | Skerven et al. |
| 2007/0260327 A1 | 11/2007 | Case et al. |
| 2007/0276428 A1 | 11/2007 | Haller et al. |
| 2007/0276432 A1 | 11/2007 | Stack et al. |
| 2008/0033574 A1 | 2/2008 | Bessler et al. |
| 2008/0065122 A1 | 3/2008 | Stack et al. |
| 2008/0097510 A1 | 4/2008 | Albrecht et al. |
| 2008/0116244 A1 | 5/2008 | Rethy et al. |
| 2008/0190989 A1 | 8/2008 | Crews et al. |
| 2008/0195226 A1 | 8/2008 | Crews et al. |
| 2008/0208355 A1 | 8/2008 | Stack et al. |
| 2008/0208356 A1 | 8/2008 | Stack et al. |
| 2008/0269797 A1 | 10/2008 | Stack et al. |
| 2008/0294179 A1 | 11/2008 | Balbierz et al. |
| 2008/0319471 A1 | 12/2008 | Sosnowski et al. |
| 2009/0018558 A1 | 1/2009 | Laufer et al. |
| 2009/0024143 A1 | 1/2009 | Crews et al. |
| 2009/0030284 A1 | 1/2009 | Cole et al. |
| 2009/0125040 A1 | 5/2009 | Hambly et al. |
| 2009/0171383 A1 | 7/2009 | Cole et al. |
| 2009/0177215 A1 | 7/2009 | Stack et al. |
| 2009/0182424 A1 | 7/2009 | Marco et al. |
| 2009/0236388 A1 | 9/2009 | Cole et al. |
| 2009/0236389 A1 | 9/2009 | Cole et al. |
| 2009/0236390 A1 | 9/2009 | Cole et al. |
| 2009/0236391 A1 | 9/2009 | Cole et al. |
| 2009/0236392 A1 | 9/2009 | Cole et al. |
| 2009/0236394 A1 | 9/2009 | Cole et al. |
| 2009/0236396 A1 | 9/2009 | Cole et al. |
| 2009/0236397 A1 | 9/2009 | Cole et al. |
| 2009/0236400 A1 | 9/2009 | Cole et al. |
| 2009/0236401 A1 | 9/2009 | Cole et al. |
| 2009/0236938 A1 | 9/2009 | Cole et al. |
| 2009/0299487 A1 | 12/2009 | Stack et al. |
| 2010/0016988 A1 | 1/2010 | Stack et al. |
| 2010/0100109 A1 | 4/2010 | Stack et al. |
| 2010/0116867 A1 | 5/2010 | Balbierz et al. |
| 2010/0204719 A1 | 8/2010 | Balbierz et al. |

FOREIGN PATENT DOCUMENTS

| | | |
|---|---|---|
| EP | 0 775 471 A1 | 5/1997 |
| EP | 1256318 A1 | 11/2002 |
| EP | 1492478 | 1/2005 |
| EP | 1 602 336 A2 | 12/2005 |
| FR | 2768324 A1 | 3/1999 |
| WO | WO 91/01117 A1 | 2/1991 |
| WO | WO 95/25468 A1 | 9/1995 |
| WO | WO 97/47231 A1 | 12/1997 |
| WO | WO 97/47231 A2 | 12/1997 |
| WO | WO 00/12027 A1 | 3/2000 |
| WO | WO 00/32137 A1 | 6/2000 |
| WO | WO 00/78227 A1 | 12/2000 |
| WO | WO 01/41671 | 6/2001 |
| WO | WO 01/45485 A2 | 6/2001 |
| WO | WO 01/49359 A1 | 7/2001 |
| WO | WO 01/66018 A1 | 9/2001 |
| WO | WO 01/85034 A1 | 11/2001 |
| WO | WO 01/89393 A1 | 11/2001 |
| WO | WO 02/060328 A1 | 8/2002 |
| WO | WO 03/017882 | 3/2003 |
| WO | WO 03/086246 | 10/2003 |
| WO | WO 03/086247 | 10/2003 |
| WO | WO 03/090633 | 11/2003 |
| WO | WO 03/094784 A2 | 11/2003 |
| WO | WO 03/094785 | 11/2003 |
| WO | WO 03/099137 A2 | 12/2003 |
| WO | WO 03/105698 A2 | 12/2003 |
| WO | WO 2004/019765 | 3/2004 |
| WO | WO 2004/019787 | 3/2004 |
| WO | WO 2004/032760 A2 | 4/2004 |
| WO | WO 2004/037064 | 5/2004 |
| WO | WO 2004/041133 | 5/2004 |
| WO | WO 2004/064680 | 8/2004 |
| WO | WO 2004/064685 | 8/2004 |
| WO | WO 2004/080336 | 9/2004 |
| WO | WO 2004/110285 A1 | 12/2004 |
| WO | WO 2005/037152 A1 | 4/2005 |
| WO | WO 2005/079673 A2 | 9/2005 |
| WO | WO 2005/096991 A1 | 10/2005 |
| WO | WO 2005/105003 | 11/2005 |
| WO | WO 2006/016894 A1 | 2/2006 |
| WO | WO 2006/055365 A2 | 5/2006 |
| WO | WO 2006/127593 | 11/2006 |
| WO | WO 2007/041598 A1 | 4/2007 |
| WO | WO 2007/041958 A1 | 4/2007 |
| WO | WO 2008/030403 | 3/2008 |
| WO | WO 2008/033409 | 3/2008 |
| WO | WO 2008/033474 | 3/2008 |

(56) References Cited

FOREIGN PATENT DOCUMENTS

| WO | WO 2008/141288 | 11/2008 |
|---|---|---|
| WO | WO 2009/011881 | 1/2009 |
| WO | WO 2009/011882 | 1/2009 |
| WO | WO 2009/086549 | 7/2009 |
| WO | WO 2009/117533 | 9/2009 |
| WO | WO 2010/054399 | 5/2010 |
| WO | WO 2010/054404 | 5/2010 |

OTHER PUBLICATIONS

Cole et al., U.S. Appl. No. 12/050,169, filed Mar. 18, 2008, U.S. Appl. No. 12/050,169, 85 pages (2008).
Stecco, K. et al., "Trans-Oral Plication Formation and Gastric Implant Placement in a Canine Model", Stecco Group, San Jose and Barosnese, Inc., Redwood City, California (2004).
Stecco, K. et al., "Safety of a Gastric Restrictive Implant in a Canine Model", Stecco Group, San Jose and Barosnese, Inc., Redwood City, California (2004).
U.S. Appl. No. 12/050,169, Cole et al., Not Published.
International Search Report from PCT Patent Application No. PCT/US2002/027177 mailed Feb. 14, 2003.
International Search Report from PCT Patent Application No. PCT/US2003/004378 mailed Aug. 13, 2003.
International Search Report from PCT Patent Application No. PCT/US2003/033605 mailed Mar. 29, 2004.
International Search Report from PCT Patent Application No. PCT/US2003/033606 mailed Mar. 29, 2004.
International Search Report from PCT Patent Application No. PCT/US2003/004449 mailed Aug. 13, 2003.
International Search Report from PCT Patent Application No. PCT/US2004/006695 mailed Sep. 8, 2004.
International Search Report from PCT Patent Application No. PCT/US2004/033007 mailed Feb. 9, 2005.
International Search Report from PCT Patent Application No. PCT/US2005/014372 mailed Jul. 28, 2005.
International Search Report from PCT Patent Application No. PCT/US2006/019727 mailed Apr. 19, 2007.
International Search Report from PCT Patent Application No. PCT/US2006/038684 mailed Feb. 14, 2007.
International Search Report from PCT Patent Application No. PCT/US2007/019227 mailed Feb. 20, 2008.
International Search Report from PCT Patent Application No. PCT/US2007/019833 mailed Feb. 20, 2008.
Felsher, et al., "Mucosal apposition in endoscopic suturing", Gastrointestinal Endoscopy, vol. 58, No. 6, pp. 867-870, (2003).
International Search Report from PCT Patent Application No. PCT/US2007/019940 mailed Mar. 14, 2008.
International Search Report from PCT Patent Application No. PCT/US2008/008726 mailed Oct. 16, 2008.
International Search Report from PCT Patent Application No. PCT/US2008/008729 mailed Aug. 18, 2009.
International Search Report from PCT Patent Application No. PCT/US2008/063440 mailed Aug. 1, 2008.
International Search Report from PCT Patent Application No. PCT/US2008/088581 mailed Feb. 26, 2009.
International Search Report from PCT Patent Application No. PCT/US2009/037586 mailed Sep. 28, 2009.
International Search Report from PCT Patent Application No. PCT/US2009/063925 mailed Jan. 12, 2010.
International Search Report from PCT Patent Application No. PCT/US2009/063930 mailed Jan. 12, 2010.

\* cited by examiner

SYSTEM AND METHOD FOR ANCHORING STOMACH IMPLANT

RELATED APPLICATIONS

This application claims the benefit of U.S. Provisional Application No. 60/844,823, filed Sep. 15, 2006.

TECHNICAL FIELD OF THE INVENTION

The present invention relates generally to the field of systems and methods for performing endoscopic surgery, and specifically to systems and methods for endoscopic anchoring of implants within the stomach.

BACKGROUND

Several of Applicant's prior applications, including WO 2005/037152, U.S. Pat. No. 6,675,809, and U.S. application Ser. No. 11/439,461, Filed May 23, 2006, (each of which is incorporated herein by reference in its entirety) describe methods according to which medical implants are coupled to tissue within the stomach. According to these applications, devices for inducing weight loss (e.g. by restricting and/or obstructing flow of food into the stomach, and/or by occupying a portion of the stomach volume and/or or by limiting absorption of nutrients by the stomach and/or small intestine) may be coupled to the stomach tissue, or to tissue tunnels or plications formed from stomach tissue.

Other types of implants may be coupled to stomach tissue, plications or other tissue structures for a variety of purposes. These implants include, but are not limited to gastric space occupiers, prosthetic valves for the treatment of gastroesophageal reflux disease, gastric stimulators, pH monitors and drug eluting devices that release drugs, biologics or cells into the stomach or elsewhere in the GI tract. Such drug eluting devices might include those which release leptin (a hormone which creates feelings of satiety), Ghrelin (a hormone which creates feelings of hunger), octreotide (which reduces Ghrelin levels and thus reduces hunger), Insulin, chemotherapeutic agents, natural biologics (e.g. growth factor, cytokines) which aid in post surgery trauma, ulcers, lacerations etc. Still other implants might be of a type which might provide a platform to which specific cell types can adhere, grow and provide biologically-active gene products to the GI tract, and/or a platform for radiation sources that can provide a local source of radiation for therapeutic purposes, or provide a platform whereby diagnostic ligands are immobilized and used to sample the GI tract for evidence of specific normal or pathological conditions, or provide an anchor point for imaging the GI tract via cameras and other image collecting devices.

The present application describes a new system and method for retaining implants within the stomach. According to the disclosed and illustrated procedure, an anchor is passed endoscopically from within the stomach through the stomach wall and is embedded in the tissue of the abdominal wall. The anchor holds the stomach wall and abdominal wall in contact with one another. Bonding occurs between the stomach wall and abdominal wall, creating a reinforced tissue region surrounding the anchor. An implant is coupled to the anchor. Although the implant experiences significant forces due to movement of the stomach and passage of food and liquid through the stomach, the anchor attachment is sufficiently strong to retain the implant without unintended detachment.

BRIEF DESCRIPTION OF THE DRAWINGS

FIGS. 1-5 are a sequence of schematic views showing a portion of a stomach wall and a portion of an abdominal wall, in which:

FIG. 1 illustrates endoscopic implantation of an anchor through the stomach wall and into the abdominal wall.

FIG. 2 illustrates the step of locking the abdominal wall and stomach wall in contact with one another.

FIG. 3 illustrates the step of coupling an implant to the anchor.

FIGS. 4 and 5 illustrate the steps of deploying the implant to its expanded state, removing the spacer and adjusting the orifice size of the implant.

DETAILED DESCRIPTION

Figure 1:
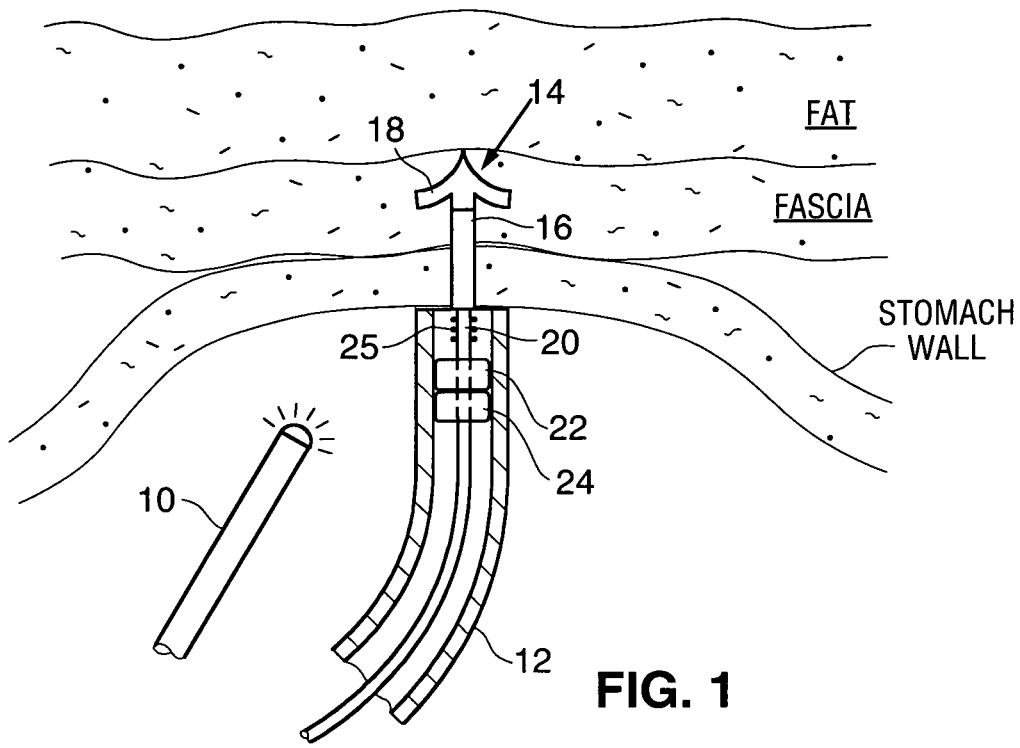

A method of implanting a gastric implant will be described in connection with FIGS. 1-5. The method will be described in the context of a restrictive device implantable within the stomach to restrict the flow of food into the stomach, although any other gastric implant including, but not limited to, those listed above may utilize a similar procedure.

At the start of the procedure, the stomach is preferably insufflated to provide working space within the stomach and to move the stomach wall closer to the abdominal wall. A flexible endoscope 10 is passed through the mouth and esophagus into the stomach. Under endoscopic visualization, the stomach is palpated until a desired location for an anchor is located. This step may be performed in a manner similar to known steps for locating a position for a percutaneous gastronomy device.

An anchor deployment catheter 12 is passed into the stomach via the esophagus and advanced to an area of the stomach wall near the target anchor site. Disposed within the anchor deployment catheter 12 is an anchor 14 having a distal end that is compressed within the catheter 12 but expandable once released from the deployment catheter 12. In one example shown in the drawings, the anchor may have a "treble hook" dart type configuration with an elongate body 16 and laterally extending barbs 18 similar to those found on a fishing lure. A tether 20 is connected to the elongate body 16 and extends through the catheter 20.

The catheter 12 is positioned with its distal end in contact with the stomach wall, and the anchor 14 is driven from the stomach through the stomach wall and into the abdominal wall, embedding the anchor in the abdominal wall. The anchor may be driven by fluid or gas pressure delivered to the anchor, or using a mandrel coupled to the anchor. Alternatively, the anchor may be compressed within a hollow needle that is advanced through the stomach wall and abdominal wall, and then released from the hollow needle once the needle is positioned within the abdominal fascia.

Figure 2:
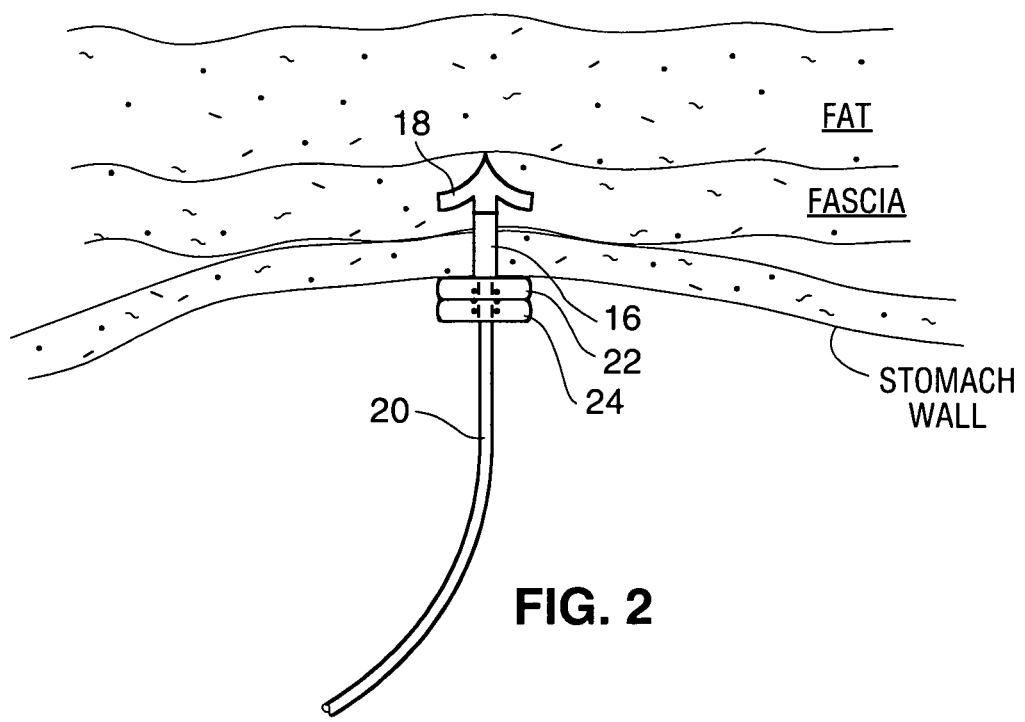
Figure 3:
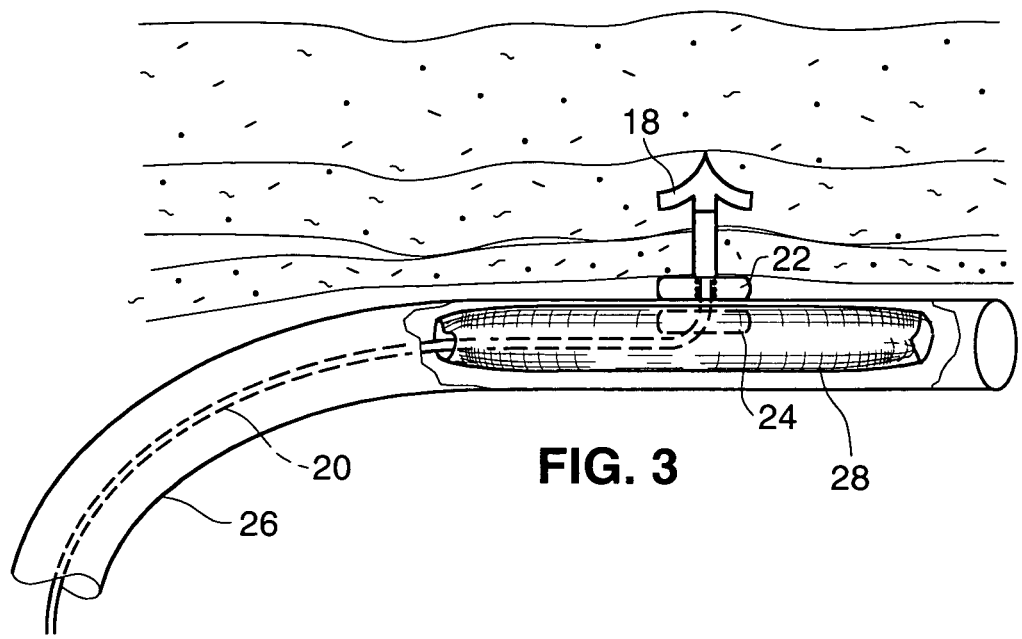

When the anchor exits the catheter 12, the barbs 18 expand to their extended positions, causing the anchor to engage with the surrounding tissue. At least a portion of the elongate body 16 remains within the stomach. With tension applied to the tether, a spacer 22 threaded onto the tether 20 is advanced into contact with the stomach wall to impart sufficient pressure against the stomach wall to draw the stomach wall and abdominal wall in contact with one another. A locking button 24, also threaded onto the tether, is advanced behind the spacer 22 and locked against the body 16 or the tether to maintain the position of the spacer 22 and to retain contact between the stomach wall and abdominal wall. Locking features for this purpose may include teeth 25 on the body 16 or tether and corresponding engaging features on the locking button (e.g. similar to a "zip-tie" arrangement). The catheter 12 is removed, leaving the anchor 14, tether 20, spacer 22 and locking button 24 in place as shown in FIG. 2.

Next, an implantation catheter 26 for a restrictive device is advanced over the tether 20 while tension is maintained on the tether. Inside the implantation catheter 26 is a tubular restrictive device 28 in a compressed position. The restrictive device 28 may be a self-expandable device retained in the compressed position by a tear-away sheath or biodegradable/absorbable sheath, or it may be one requiring active expansion using a balloon or other expandable device positioned within its lumen.

The restrictive device 28 is anchored to the locking button 24, preferably without deploying the restrictive device 28 to its expanded position. Delaying expansion of the restrictive device 28 is preferred because it allows the anchor attachment to heal and strengthen before it is subjected to the increased stresses imparted as a result of food flowing through the restrictive device. The implantation catheter 26 is withdrawn from the body and the tether 20 is cut or removed from the anchor.

Figure 4:
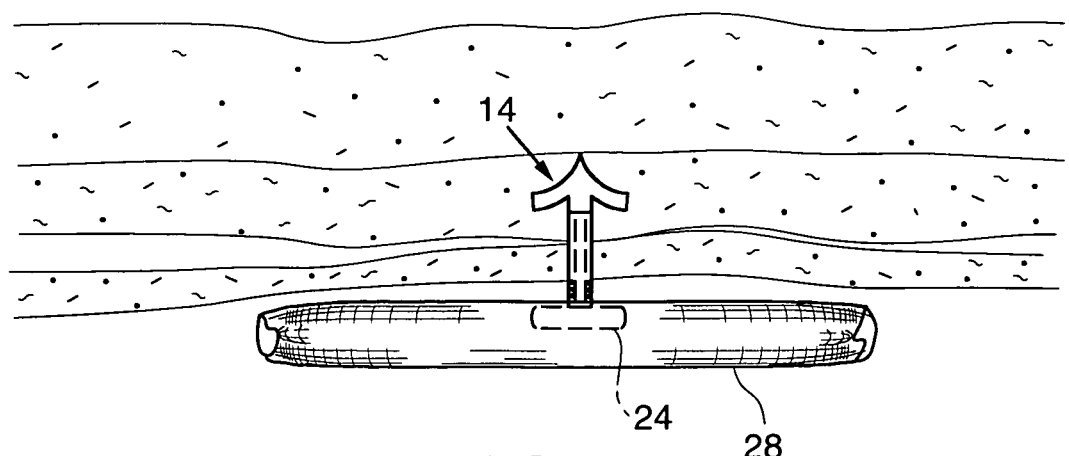
Figure 5:
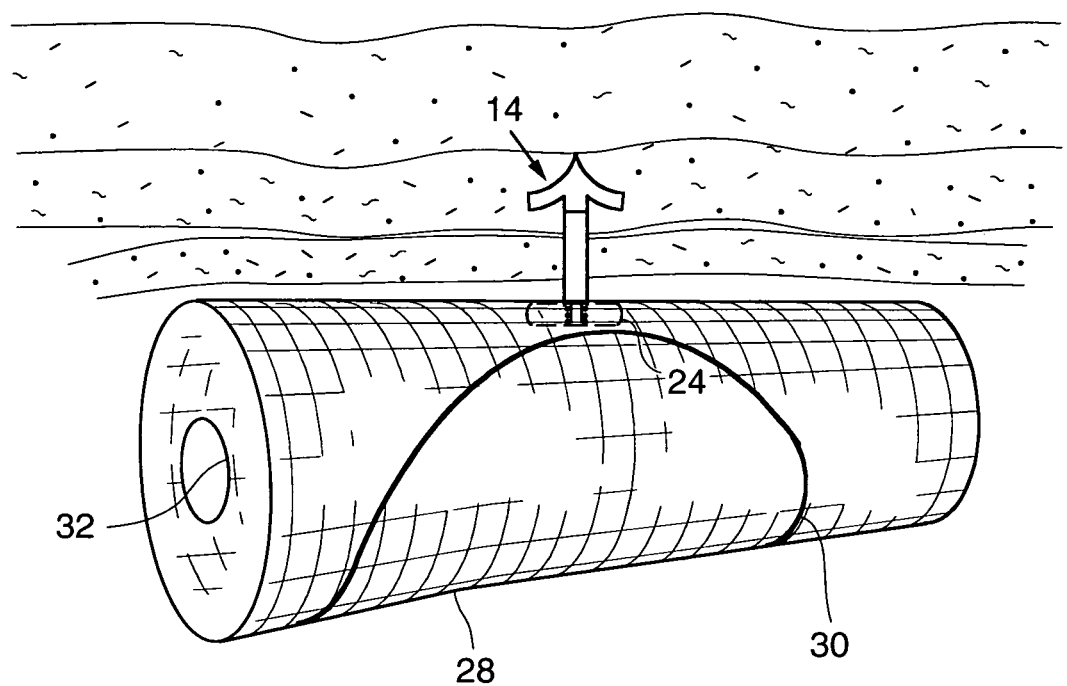

After an appropriate healing time, which may be on the order of five days, flexible endoscope 10 is advanced back into the stomach. Associated instruments are used to remove the spacer 22, leaving a gap between the locking button 24 and the stomach wall as shown in FIG. 4. Removing the spacer 22 minimizes the likelihood or erosion of the stomach wall by the spacer. In one embodiment, the spacer might be have a thickness of approximately 3 cm or more, thus leaving a gap of at least 3 centimeters between the locking button 24 and the stomach wall upon removal of the spacer. The restrictive device 28 is deployed to its expanded position as shown in FIG. 5. The orifice size (e.g. the cross-sectional area of the proximal or distal orifice 32 and/or lumen) of the restrictive device 28 is adjusted as needed to provide a desired amount of restriction sufficient to lead to an appropriate weight loss for the patient. Some methods for controlling the orifice size of the restrictor are disclosed in Applicant's U.S. Application 2004-0158331, which is incorporated herein by reference. The restrictive device 28 may include one or more stabilizing bars/struts 30 to maintain stability of the device within the stomach and to keep the proximal orifice of the implant oriented towards the esophagus for receipt of ingested food.

The disclosed system can be packaged with instructions for use instructing the user to use the system according to methods disclosed herein.

It should be recognized that a number of variations of the above-identified embodiments will be obvious to one of ordinary skill in the art in view of the foregoing description. Accordingly, the invention is not to be limited by those specific embodiments and methods of the present invention shown and described herein. Rather, the scope of the invention is to be defined by the following claims and their equivalents.

All patents and applications referred to herein, including for purposes of priority, are incorporated herein by reference.

We claim:

1. A method of anchoring an implant in a patient's stomach, comprising:
   introducing transorally into the stomach an anchor, wherein the anchor includes an expandable head at a distal end;
   passing the head of the anchor into a wall of the stomach in a contracted condition within a medical device, wherein the passing step includes placing the medical device within the stomach and piercing the wall of the stomach with the medical device;
   positioning the medical device within an abdominal fascia;
   after the positioning step, releasing the anchor from the medical device;
   expanding the head to an expanded condition to attach the anchor relative to the stomach wall;
   advancing a spacer towards the anchor and into contact with the stomach wall;
   positioning the implant within the stomach such that the spacer is positioned between the implant and the stomach wall; and
   removing the spacer from the patient.

2. The method of claim 1, wherein the implant is a flow restrictive device.

3. The method of claim 1, wherein the implant is a gastric space occupier.

4. The method of claim 1, wherein the anchor is coupled to a tether, and further comprising the steps of:
   advancing an attachment member over the tether towards the anchor;
   coupling the attachment member to the anchor;
   advancing the implant over the tether towards the attachment member;
   coupling the implant to the attachment member; and
   removing the tether from the anchor.

5. A method of anchoring an implant in a subject having a stomach, comprising:
   placing within the stomach, a catheter having a hollow needle at a distal end, wherein the catheter includes an anchor with an expandable head;
   piercing a wall of the stomach using the hollow needle;
   releasing the anchor through the needle to transform the head to an expanded condition such that the head becomes fixed relative to a wall of the stomach, wherein said releasing step includes positioning the catheter needle within an abdominal wall before releasing the anchor from the needle;
   advancing a spacer towards the anchor and into contact with the stomach wall;
   positioning the implant within the stomach such that the spacer is positioned between the implant and the stomach wall; and
   removing the spacer from the subject.

6. The method of claim 5, wherein the spacer is configured to be advanced along a tether towards the anchor.

7. The method of claim 5, wherein the implant is a flow restrictive device.

8. The method of claim 5, wherein the implant is a gastric space occupier.

9. The method of claim 5, wherein the anchor is coupled to a tether, and further comprising the steps of:
   coupling an attachment member to the anchor;
   advancing the implant over the tether towards the attachment member;
   coupling the implant to the attachment member; and
   removing the tether from the anchor.

10. A method of securing an implant to a patient's stomach, comprising:
    introducing transorally into the patient's stomach, an anchor having an expandable head at a distal end, an attachment member for attachment of the implant to the anchor, and a tether connecting said anchor and attachment member;
    passing the head of the anchor into a wall of the stomach such that the head becomes fixed relative to the wall of the stomach;
    advancing the attachment member over the tether toward the anchor;

coupling the attachment member to the anchor;
advancing the implant over the tether towards the attachment member;
coupling the implant to the attachment member; and
after coupling the implant to the attachment member, leaving a gap between the implant and the stomach wall.

11. The method of claim 10, wherein said introducing step includes placing within the stomach, a catheter having a hollow, distal-end needle, where the anchor is held within the catheter with the head in a retracted condition, and said passing step includes piercing the stomach wall using the hollow needle and releasing the anchor from the needle, wherein the head assumes an expanded condition.

12. The method of claim 11, wherein said passing step further includes positioning the needle within an abdominal wall before releasing the anchor from the needle.

\* \* \* \* \*